United States Patent [19]

Noorlander

[11] Patent Number: 4,670,263

[45] Date of Patent: Jun. 2, 1987

[54] NONTOXIC, GERMICIDE, AND HEALING COMPOSITIONS

[76] Inventor: Daniel O. Noorlander, 508 W. 630 South, Orem, Utah 84057

[21] Appl. No.: 798,353

[22] Filed: Nov. 15, 1985

Related U.S. Application Data

[63] Continuation of Ser. No. 566,512, Dec. 29, 1963, abandoned.

[51] Int. Cl.⁴ ............................................. A61K 35/78
[52] U.S. Cl. .......................... 424/195.1; 424/DIG. 13
[58] Field of Search ..................... 424/195.1, DIG. 13

[56] References Cited

U.S. PATENT DOCUMENTS

| | | | |
|---|---|---|---|
| 3,930,000 | 12/1975 | Margraf | 424/245 |
| 4,264,592 | 4/1981 | Xhajanka | 424/195 |
| 4,318,906 | 3/1982 | Llopart | 424/195 |

OTHER PUBLICATIONS

E. F. Steinmetz, Code X Vegetabilis, #1111, Symphytam Officinale, 1957.
Merck Index, 9th ed., #7644, Propylene Glycol; #240, Allantoin; and #2137, Chlorophyll, 1976.
I. Stone, "The Healing Factor", Crosset & Dunlap, N.Y., pp. 164–166, 178 and 179, 1972.
Martindale, The Extra Pharmacopoeia, ed. J. Reynolds, 1982, pp. 708–709.

*Primary Examiner*—Johnnie R. Brown
*Assistant Examiner*—John W. Rollins
*Attorney, Agent, or Firm*—Thorpe North and Western

[57] ABSTRACT

Nontoxic, germicide, and healing composition are disclosed comprising propylene glycol, allantoin and water. The composition may also include ascorbic acid and/or a member selected from the group consisting of chlorophyll, carotene, and mixtures thereof.

6 Claims, No Drawings

NONTOXIC, GERMICIDE, AND HEALING COMPOSITIONS

This application is a continuation of application Ser. No. 566,512, filed Dec. 29, 1983, now abandoned.

BACKGROUND OF THE INVENTION

1. Field

The invention relates to nontoxic, germicide and healing compositions, and in particular to such compositions which are adapted to topical application.

2. State of the Art

Comfrey (*Symphytum officinole*) has been reported in old herbal books as far back as 200 A.D. as a valuable medicinal herb to encourage epethelial formation in wounds, ulcers, and osteomylelites. An evaluation of the plant by many investigators has disclosed that allantoin, a diureide of glycoxylic acid is the active ingredient found in the comfrey plant that increases the granulation of damaged tissue in the healing process. Allantoin can also be formed by the oxidation of uric acid. Extensive use, however, of the comfrey plant or of its active ingredient allantoin has not been emplloyed in either human medical treatment or in the area of veterinary medicine.

OBJECTIVES

A principal objective of the present invention is to provide an effective germicide and healing composition which can be used in human and veterinary medicine, particularly as a sterile, topical dressing for skin infections, burns, and ulcers. An additional objective of the present invention is to provide a composition which is active to killing infectious microorganisms such as Staphylococcal and Streptococcal bacteria. A particular objective of the present invention is to provide a nontoxic, topical dressing which kills many types of pathogenic bacteria on the surface of skin tissue while at the same time effecting a rapid healing of the damaged tissue. Another objective is to provide a nontoxic, germicide, and healing composition which can be used as a topical dressing for application to dairy cattle in the treatment among others of mastitis and bovine metritus. A further objective was to provide a nontoxic, germicide, and healing composition which can be infused into the udder and the uterus of dairy cattle in the treatment of mastitis and bovine metritus, respectively. An additional objective was to provide a nontoxic, germicide, and healing composition comprising an extract of the comfrey plant made by extracting the leaves and stems of the comfrey plant with propylene glycol.

SUMMARY OF THE INVENTION

The above objectives are achieved in accordance with the present invention by providing a novel, nontoxic, germicide, and healing composition comprising propylene glycol, allantoin, and water. The concentration of the propylene glycol is at least about 25% by weight, with the concentration of allantoin being from about 0.02% and 1% by weight. In a preferred embodiment of the invention, the nontoxic germicide, and healing composition further includes from about 0.05% to 1% by weight ascorbic acid. In an additional preferred embodiment of the invention, the nontoxic, germicide, and healing composition further includes from about 0.005% to 0.05% by weight of a member selected from the group consisting of chlorophyll, carotene, and mixtures thereof. In another preferred embodiment of the invention, the nontoxic, germicide, and healing composition containing the basic ingredients, i.e., the propylene glycol, allantoin, and water, further contains both the ascorbic acid component and the member selected from the group consisting of chlorophyll, carotene, and mixtures thereof.

A skin ointment can be made from any of the above-mentioned embodiments of the composition of the present invention by mixing about 0.75 to 2 parts by weight mineral oil and about one part by weight lanolin to any one of the compositions mentioned in the preceeding paragraph.

The composition containing the propylene glycol, allantoin, water, and other diseretionary ingredients mentioned above, in accordance with the present invention can be produced by simply mixing the separate ingredients. In a particularly preferred embodiment of the invention, however, the composition containing the basic ingredients, i.e., the propylene glycol, allantoin, and water is made by forming an extract from the comfrey plant. The extract is produced by soaking the leaves and stems of the comfrey plant in propylene glycol, wherein the ratio of comfrey plant to propylene glycol is about 10 to 24 ounces green comfrey plant to one gallon of propylene glycol or about 2 to 8 ounces of dried comfrey plant to one gallon of propylene glycol. The propylene glycol can be heated to a temperature of up to about 210° F. if so desired to increase the rate of extraction of the allantoin, chlorophyll, and mucin from the stems and leaves of the comfrey plant. After a time sufficient for the bulk of the allantoin, chlorophyll, and mucin to be extracted from the stems and leaves of the comfrey plant, a concentrated, mother liquor solution is filtered from the spent solids, and from about 10% to 75% water by weight of the resulting diluted extract solution is added to the mother liquor solution. Allantoin can then be added to the diluted extract solution in an amount of about 0.1% to 0.2% by weight of the diluted extract solution to thereby yield a composition containing at least 0.1% and up to about 1% by weight allantoin.

The extract obtained by the method mentioned in the above paragraph will, of course, contain chlorophyll and possibly carotene which has been extracted from the stems and leaves of the comfrey plant. However, it has been found advantageous to add a member selected from the group consisting of chlorophyll, carotene, and mixtures thereof to the diluted extract solution in an amount of about 0.005% to 0.25% by weight of the diluted extract solution. Ascorbic acid can be added to the diluted extract solution or to the diluted solution to which the additional amounts of chlorophyll and/or carotene have been added. The amount of ascorbic acid added to the diluted extract solution is preferably between about 0.05% and 1% by weight of the diluted extract solution.

A skin ointment can be made from any of the extract solutions of the two proceeding paragraphs by mixing about 0.75 to 2 parts by weight mineral oil and about one part by weight lanolin to any one of the extracts.

DETAILED DESCRIPTION OF THE PREFERRED EMBODIMENTS

Additional objects and features of the invention will become apparent from the following detailed description which describe particular, preferred embodiments of the invention representing the best mode presently contemplated of carrying out the invention.

In accordance with the invention, a nontoxic, germicide, and healing composition is provided comprising propylene glycol, allantoin, and water. The concentration of propylene glycol is at least 25% by weight and preferably between about 25% and 90% by weight. The concentration of allantoin is between about 0.02% and 1% by weight and preferably between about 0.1% and 0.5% by weight. It has been unexpectedly found that the composition containing propylene glycol, allantoin, and water is effective in killing many types of bacteria when applied to skin or tissue in which the bacteria are found. In addition, the application of the composition accelerates the healing process for cuts, cracks, etc. in the skin tissue of animals and humans.

In a particular preferred embodiment of the composition of the present invention, from about 0.05% to 1% by weight ascorbic acid is included therein, preferably from about 0.1% to 0.5% by weight. The ascorbic acid has been found to produce a synergistic effect upon the kill rate of bacteria by the composition. For example, a composition containing 75% by weight propylene glycol and 0.02% to 1% by weight allantoin has been found to be effective in killing essentially all staphylococcal bacteria in controlled tests when the composition has been brought in contact with the bacteria for a time period within one to two hours. The same composition further containing about 0.1% ascorbic acid was found to be effective in killing essentially all staphylococcal bacteria in controlled tests when the composition has been brought in contact with the bacteria for a time period within about 35 minutes. Ascorbic acid solutions with a concentration of about 0.1% by weight ascorbic acid were found to take one to two hours to kill the staphylococcal bacteria. Higher concentration of ascorbic acid, up to about 2% by weight, will kill the bacteria more rapidly tha the lower concentration of ascorbic acid, but the higher concentrations of ascorbic acid tend to be harmful to skin tissue and other tissues of both animals and humans.

It has also been found that from about 0.005% to 0.05% by weight of a member selected from the group consisting of chlorophyll, carotene and mixtures thereof can be added to either the composition containing the propylene glycol, allantoin, and water or the composition containing propylene glycol, allantoin, water and ascorbic acid. The chlorophyll and/or carotene also has a synergistic effect on the bacterial kill rate of the compositions. Carotene is any of three red or orange-colored isomeric hydrocarbons found in carrots and certain other vegetables and which is changed into vitamin A in the body. In a particularly preferred embodiment the composition of the present invention comprises about 25% to 90% by weight propylene glycol, about 0.02% to 1% by weight allantoin, about 0.05% to 1% by weight ascorbic acid, and from about 0.005% to 0.5% by weight of a member selected from the group consisting of chlorophyll, carotene, and mixtures thereof.

The comfrey plant contains many of the ingredients of the composition of the present invention, and it has been found that a particularly preferred embodiment of the composition of the present invention can be produced by extracting the leaves and stems of the comfrey plant with propylene glycol. The leaves and stems of the comfrey plant are soaked in or otherwise extracted with propylene glycol. The ratio of comfrey plant to propylene glycol is about 10 to 24 ounces green comfrey plant to one gallon of propylene glycol or about 2 to 8 ounces of dried comfrey plant to one gallon of propylene glycol. The temperature of the propylene glycol can be elevated up to 210° F. or thereabouts to increase the rate of extraction of the ingredients of the comfrey plant. The extracted solution is then filtered from the spent comfrey plant solids, and the filtered solution is diluted with about 10% to 75% water by weight of the diluted solution. Allantoin is then added to the diluted solution in an amount of about 0.1% to 0.2% by weight of the diluted solution to thereby yield a preferred embodiment of the composition of the invention.

Among the ingredients which are extracted from the comfrey plant are mucin, carotene, chlorophyll, Vitamin C, and allantoin. As mentioned above, supplemental allantoin is added to the extract. Supplemental amounts of carotene, chlorophyll, and Vitamin C can also be added to the extract. Preferably, from about 0.005% to 0.025% of a member selected from the group consisting of chlorophyll, carotene, and mixtures thereof is added, by weight, to the extract. Ascorbic acid is also preferably added to the extract in an amount of from about 0.05% to 0.1% by weight of the extract.

One of the major advantages of the composition of the present invention is that it provides for an alternative method of treating dairy animals for mastitis and bovine metritus whereby antibiotics are not required. Without the use of antibiotics, and in view of the fat that the present composition consists of oil food grade or edible ingredients, the milk obtained during treatment of the dairy animals need not be discarded. Using the extract solution of from the comfrey plants as described above (comfrey extract in propylene glycol base with the supplemental amounts of allantoin and chlorophyll or carotene or both), extensive testing was done to test the toxicity, bacteriocide, and healing properties for human and animal diseases.

It was found that when the teats of dairy animals were treated by topical application to the teats, as well as infusion of the extract into the udder, mastitis which had not developed to the chronic stage could be cured with two treatments of the extract. Teats which had been chronically infected did not respond as well. Amputated udders from the treated animals indicated that deep, well developed scar tissue retarded contact of the extract with the causative organisms causing the mastitis. Mastitis is a major bacterial disease of dairy animals due to several types of bacteria including Pseudomonas, Staphylocaccus and Streptococcus. Laboratory experiments have shown conclusively that the compositions of this invention are very effective in killing those type bacteria.

In one herd of 125 cows, seven of the animals had teat ends that were ruptured and cracked. The dairymen had been using iodine preparations in an effort to heal the teats. In just two days, by dipping the teats in the composition of the invention, the teat ends of the seven cows heald. A second herd reported similar healing properties for the composition. Cows with chapped teats and skin lesions healed in less than three days, and the tissue became soft and smooth due to ingredients in the composition. A deep cut on the surface of the teat of one cow healed in less than five days after treatment. Treatment of cuts on horses have responded very well, with prevention of the development of "proud flesh" which often accompanies the healing of such cuts.

Wounds and burns on experimental animals healed 20 to 24 hours sooner when treated with the composition of the invention as compared to control animals which were not treated.

The composition of the invention has also been tested extensively in the treatment of metritis of dairy cattle. The normal treatment was 90 ml of the composition infused into the uterus every day for three days. This method was very effective in treating the post-partum uterus. There was no visible irritation to the mucus membrane or epithelial tissue. A beneficial effect on the endometrium was common.

Laboratory testing has demonstrated that the compositions of the invention have excellent kill properties as to various bacteria. Staphylococcal, streptococcal, yeast, coliform, pseudomona, and some fungal microorganisms could be killed in as litle as 10 to 30 minutes. Rod shaped organisms with spores are not killed as rapidly as the spherical shaped streptococcal and staphylococcal bacteria, but the composition does act to kill such organisms.

The compositions of the invention have been used very successfully on skin infections such as diaper rash, dermatitis, and chapped and damaged skin. Babies infected with yeast, bed sores, diaper rash, etc., for the most part cleared up in less than three days. The compositions of the invention have also been used with remarkable results on skin fungus and acne.

Ointments containing the nontoxic germicide, and healing composition of the present invention can be provided and are advantageous when used on tender skin, such as when used for diaper rash. The ointments can be prepared using mineral oil, lanolin and mixtures thereof as a base in which the various embodiments of the composition of the invention as discussed hereinabove can be incorporated. It has been found that the compositions of the invention can be prepared with the mineral oil and lanolin bases without diminishing the bacteriocidal properties of the compositions.

A preferred embodiment of an ointment in accordance with the present invention can be prepared by mixing 0.75 to 2 parts by weight mineral oil, about one part by weight lanolin, and about 2 to 3 parts by weight of any one of the nontoxic, germicide, and healing compositions encompassed by the present invention.

Although preferred embodiments of the compositions and preparations of the present invention have been described, it is to be understood that the present disclosure is made by way of example and that various other embodiments are possible without departing from the subject matter coming within the scope of the following claims, which subject matter is regarded as the invention.

I claim:

1. A nontoxic, germicide, and healing composition which comprises an extract which is produced by the steps of: soaking the leaves and stems of the comfrey plant in propylene glycol, wherein the ratio of comfrey plant to propylene glycol is about 10 to 24 ounces green comfrey plant to one gallon of propylene glycol or about 2 to 8 ounces of dried comfrey plant to one gallon of propylene glycol; filtering the resulting solution; diluting the filtered solution with about 10% to 75% water by weight of the diluted solution; adding allantoin to the diluted solution in an amount of about 0.1% to 2% by weight of the diluted solution; and adding ascorbic acid to the diluted solution in an amount of about 0.5% and 1% by weight of the diluted solution to thereby yield said extract.

2. A nontoxic, germicide and healing composition in accordance with claim 1, wherein a member selected from the group consisting of chlorophyll, carotene, and mixtures thereof is added to the extract in an amount of 0.005% to 0.025% by weight of the extract.

3. A skin ointment comprising about 0.75 to 2 parts by weight mineral oil, about one part by weight lanolin, and about 2 to 3 parts by weight of the nontoxic, germicide, and healing composition of claim 1.

4. A method of treating bovine teats for mastitis comprising topically applying an effective amount of the composition of claim 1 to the teats of the cow being treated.

5. A method in accordance with claim 4 wherein said composition is also infused into the teats and udder of the cow being treated.

6. A method of treating metritis in dairy cattle comprising infusing an effective amount of the composition of claim 1 into the uterus of the cow being treated.

* * * * *